United States Patent [19]

Ly

[11] Patent Number: 4,654,310

[45] Date of Patent: Mar. 31, 1987

[54] INSTRUMENTLESS QUANTITATIVE ANALYSIS SYSTEM

[76] Inventor: Uy-Vu Ly, P.O. Box 32564, San Jose, Calif. 95152

[21] Appl. No.: 569,891

[22] Filed: Jan. 10, 1984

[51] Int. Cl.$^4$ .................. G01N 21/77; G01N 21/78; G01N 33/48; G01N 33/52

[52] U.S. Cl. .................. 436/164; 422/56; 422/58; 422/61; 435/805; 436/95; 436/169

[58] Field of Search .......... 435/805; 436/810, 169, 436/174, 95, 164; 422/56, 57, 58, 61

[56] References Cited

U.S. PATENT DOCUMENTS

| | | | |
|---|---|---|---|
| 3,272,319 | 9/1966 | Brewer | 422/61 |
| 3,449,081 | 6/1969 | Hughes | 422/61 |
| 3,723,064 | 3/1973 | Liotta | 422/56 |
| 3,917,453 | 11/1975 | Milligan et al. | 422/56 |
| 3,964,871 | 6/1976 | Hochstrasser | 435/805 X |
| 3,983,005 | 9/1976 | Goodhue et al. | 435/805 X |
| 4,281,062 | 6/1981 | Kallis | 422/56 X |
| 4,330,229 | 5/1982 | Cerami | 422/56 |
| 4,452,887 | 6/1984 | Kitajima et al. | 435/805 X |

FOREIGN PATENT DOCUMENTS

| | | | |
|---|---|---|---|
| 3211167 | 9/1983 | Fed. Rep. of Germany | |
| 7243677 | 11/1972 | Japan | 422/56 |
| 0016692 | 2/1978 | Japan | 422/56 |

Primary Examiner—Barry S. Richman
Assistant Examiner—C. M. Delahunty
Attorney, Agent, or Firm—Ciotti & Murashige

[57] ABSTRACT

A method for generating a series of digital responses to the presence of a given concentration of analyte in a test sample is described. The responses are obtained by providing varying levels of components of a competing reaction with constant levels of components of a control reaction. The pattern of digital responses permits a direct reading of the level of analyte in the test sample. Analytes may be either substrates for enzyme reactions, or may be, themselves, enzymes.

14 Claims, 4 Drawing Figures

INSTRUMENTLESS QUANTITATIVE ANALYSIS SYSTEM

BACKGROUND

The field of the present invention is the facile analysis of analytical samples. More particularly, the present invention relates to assessment of the quantity of a desired analyte using a catalyzed indicator reaction in competion with a second catalyzed reaction utilizing the same substrate as the indicator reaction.

The need for quantitative determination of the concentration of a substance of interest in a test sample is widespread and varied in application. Such need arises prominently in connection with clinical laboratory tests, quality control in the production of any mixture of materials, for example, food, agricultural, industrial, or other mixtures; and in analytical assessment of, for example, waste products such as industrial or municipal waste. Methods of quantitation are varied but generally involve generation of some detectable material such as a colored substance, a substance absorbing ultra-violet or infrared light at a particular wavelength, a fluorescent material, or, in general, a material which absorbs or generates radiation of a particular energy. Such radiation levels can be detected through instrumentation using instruments of complexity ranging from that of a simple colorimeter, or even a color comparator chart, to sophisticated variable wavelength specific infrared spectrometers. Additional detection methods rely on characteristic properties of either the substance to be determined or of a material into which it can be converted, which are assessed by more complex means such as, for example, mass spectroscopy, nuclear magnetic resonance spectroscopy, or stimulated emission of X-radiation.

The expense and sometimes the complexity of these analytical procedures are, of course, proportional to the sophistication of the instrumentation required, (although a highly complex instrument can sometimes eliminate many operator manipulations). Especially for preliminary screening tests, and for tests which are useful to individual consumers, it would be desirable to formulate testing procedures which obviate the need for expensive instrumentation and which are simple to perform. The present invention provides a method for quantitation of desired analytes which eliminates the need for such complication and expense. It provides a testing method which is useable unaided by instrumentally based analog measurements and gives essentially a digital readout useable to virtually anyone.

The method of the present invention is grounded in the competition for substrate by each of a pair of catalysts. Other procedures have recently been devised which depend on some sort of competitive reactivity, but which, nevertheless, often require quantitation using dedicated equipment. For example, the method of radioimmunoassay (RIA) capitalizes on competition between the desired analyte in a sample and supplied labeled analyte for the same antibody. By assessing the quantity of labeled material bound to antibody, the level of competition offered by the analyte in the sample can be assessed. This method requires that the operator use radioactive materials, and complex counting equipment is required. Similar procedures also based on competition for a specific immunoglobulin utilize a colorimetric detection system based on an enzymatic reaction. In such techniques, commonly known as ELISA or EMIT, competition from the analyte results in the release of enzyme an indicator reaction from an inactivating antibody.

In the present invention, however, the amount of analyte available for an indicator reaction is dependent on the amount of catalyst for a competing reaction present. By varying the amount of competing reaction catalyst the amount of analyte remaining can be left at a detectable level or not. As the amount of competing catalyst can be determined by the will of the experimenter (or by a series of preset levels chosen by the manufacturer), no instrumentation is required for its quantitation.

SUMMARY OF THE INVENTION

In one important aspect, the invention provides a method for quantitating the concentration of any desired analyte by assessing a pattern of yes/no responses. Since this is a digital result, these results can be read using a series of, for example, test papers or pattern on a matrix, rather than by use of expensive instrumentation. The method which is represented by this aspect of the invention comprises testing a sample by means of, for example, an indicator reaction at varying levels of competition with a competing reaction which competes for the same analyte. Thus, one can assess by a series of positive or negative responses, at what level of competition the analyte begins to lose. More analyte will require more competition before it ceases to prevail. Therefore, this approach, with suitable calibration, provides a measure of the concentration of the substance to be measured.

Briefly and more specifically described, in one illustration of the method of the invention, the sample to be analyzed for a substrate analyte is divided into portions and treated with identical quantities of reagents and appropriate catalyst which will carry out a reaction of the analyte leading to a visible or otherwise detectable response (an "indicator" reaction). The portions are also treated with varying amounts of a catalyst which controls the rate of a second reaction which uses up the analyte substance to be measured in competition with the indicator reaction. At low concentrations of the catalyst for the competing reaction, sufficient analyte will remain to give a positive response in the indicator reaction. At higher concentrations of competing catalyst, concentration of analyte will drop below the level necessary for the indicator reaction to be detectable. The point of changeover from a positive to negative result provides an index to the concentration of analyte.

In another illustration, the analyte is itself a catalyst (enzyme). This may either catalyze the indicator reaction, which reaction is then obtained by supplying a constant quantity of substrate, or it may catalyze a non-indicating "control" reaction which uses up substrate for a competing reaction—in this case, the competing reaction must be "indicating".

In another variation, the analyte to be measured generates a "secondary analyte" by virtue of a suitable analyte-specific reaction. This secondary analyte replaces the analyte to be measured as the substrate for the competing control/indicator and competing reactions. Thus, in this variation, the sample to be analyzed is again divided into portions, and, in addition to the components added as described above, reaction components specific for the desired analyte are added to the reaction mixture. This confers specificity on the test, as well as providing the secondary analyte which forms the substrate for the competing reactions. By virtue of this variation, a standard competition pattern can be applied to a number of desired analytes as long as these analytes generate the same secondary analyte. The specificity in this embodiment is conferred by the nature of this conversion reaction into secondary analyte.

Thus, in one aspect the invention relates to a method for determining the concentration of a desired analyte (an enzyme or a substrate) by adding to a series of samples constant amounts of the reaction components for a control reaction and variable amounts of catalyst for a competing reaction, where one of the two reactions is also an indicator reaction. In instances where the analyte is a substrate, it is preferred that the control reaction be the indicator reaction.

In a second aspect, the invention relates to using as a substrate analyte in the foregoing method a secondary analyte which is generated by an analytespecific reaction.

In other aspects, the invention relates to kits which contain the appropriate concentrations of the reagents used in the foregoing methods. In still other aspects, such kits will include means for separating the solution to be analyzed into portions and of contacting these portions with the proper reagents; in still further aspects, the invention relates to support matrices which provide direct reading capability in preset pattern of reaction variations, as is described by the foregoing method of the invention.

DETAILED DESCRIPTION

A. Definitions

As used herein, "analyte" or "desired analyte" refers to the material whose concentration is to be measured. In the case of clinical tests, for example, such analytes might be glucose, cholestrol, ammonia, urea, triglycerides, amino acids, bacterial cell wall components, antibodies, or other materials which can be substrates for chemical reactions accelerated or controlled by enzymes or other catalysts which are specific to them. For other applications, analytes might include pesticides present in waste water samples, specific chemical products which form part of atmospheric pollution, specific intermediates in chemical conversion manufacturing processes and numerous other materials which are of interest in the context of a wide variety of applications. Where the analyte is an enzyme, examples of such analytes include phosphatase, glucose oxidase, urease, or any enzyme for which the substrate can be consumed by another, competing enzyme.

"Sample" refers to the material in which the concentration of the analyte is to be measured. Such samples may also be of almost infinite variety—from clinical samples such as blood and urine or derivatives thereof, to in vivo intracellular environments, to sewage treatment affluents and the like. As used herein, the term "sample" refers to a quantity of material, however prepared or found, which is to be assayed for the concentration of analyte present.

"Secondary analyte" refers to a material generated as a product of the reaction involving the desired analyte either as a substrate or as a catalyst. The specificity is controlled by the enzyme/substrate specificity of this reaction. Thus, for example, any desired analyte which can be treated as a substrate by a catalyst controlling a reaction which generates hydrogen peroxide can be quantitated by the method of the invention by first effecting the hydrogen peroxide-producing conversion essentially to completeness. The specificity of the catalyst for the generation of hydrogen peroxide will limit the assay to the desired analyte. For example, both cholesterol and glucose are capable of producing hydrogen peroxide when oxidized in the presence of air, glucose in the presence of glucose oxidase and cholesterol in the presence of cholesterol oxidase. Either glucose or cholesterol could thus be assayed by first using the primary analyte in the presence of a suitable catalyst to generate hydrogen peroxide, the secondary analyte.

Conversely, if the analyte were an enzyme, such as glucose oxidase, glucose would be added to permit the peroxide generation to take place.

"Indicator reaction" refers to a reaction which directly or indirectly depends on the concentration of the desired analyte or secondary analyte, and which produces a substance which is detectable. In its simplest embodiment, such product could be a material which is detectable by means of simply viewing its color. Such indicator reactions may take place in more than one step, and "reaction" in the singular is intended to include both single step conversions and multiple step conversions as the case may be.

"Control reaction" refers to a reaction involving the desired or secondary analyte for which the reaction components are added to the mixture in constant amount. For direct substrate analysis, the "control" reaction is frequently also the "indicator" reaction. For enzyme analytes, the "control" reaction usually utilizes the same substrate as a competing, indicator reaction.

"Competing reaction" refers to a reaction which utilizes as a substrate the same substrate analyte as the control reaction or uses the substrate supplied as a reagent for the control reaction where the analyte is itself an enzyme, and which is catalyzed by a "competing catalyst". Thus, in the illustration where the indicator reaction is also the control reaction, the primary or secondary analyte as the case may be, will be successful in generating the detectable product of the indicator reaction if and only if it is present in sufficient amounts to avoid being consumed by the competing reaction or, in the case where the analyte itself is an enzyme, where the analyte enzyme is of sufficient concentration to dominate the competitor.

"Specific analyte reaction" refers to a preliminary specific reaction which uses stoichiometrically a desired analyte or which is catalyzed by an enzyme analyte to generate a secondary one, which secondary analyte can serve as the substrate for both the control and competing reactions. The specific analyte reaction for a substrate analyte is catalyzed by a suitable enzyme or other catalyst which is sufficiently specific for the desired analyte to permit its conversion to the secondary analyte while failing to catalyze similar reactions utilizing contaminating materials in the sample. For an enzyme analyte, the reaction utilizes added substrate for the specific enzyme analyte.

"Reaction components" refers to catalyst(s) and/or such reactants as are not already present in the samples to be tested required to carry out the reaction in question. Thus, for example, if the analyte is the substrate for the indicator reaction, "indicator reaction components" refers to the enzyme and other reactants; if the analyte is an enzyme, the phrase "control reaction components" refers to the substrate and any other reactants for the control reaction.

B. General Description of the Method

Figure 1:
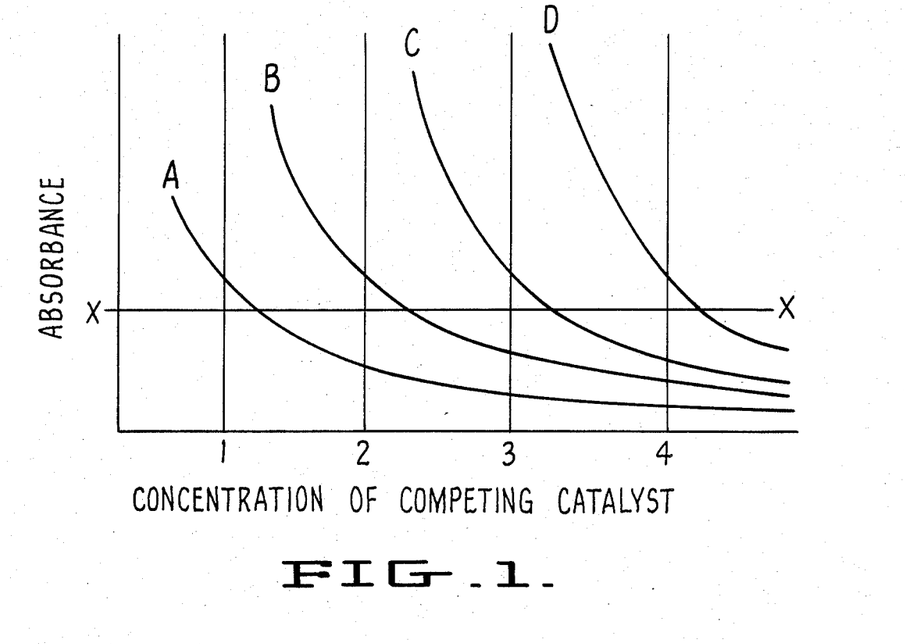
FIG. 1 shows the variation of absorbance with competing catalyst concentration for various analyte concentrations.

The principle upon which the method of the present invention is based can best be described in terms of a hypothetical set of results for one embodiment diagrammed in FIG. 1. In this illustration, the control reaction is the indicator reaction as well. The graphical representation in FIG. 1 is a plot of absorbance (y-axis) of a color product formed in an indicator reaction as a function of competing catalyst concentration (x-axis) for a series of four analyte concentrations A(lowest)-D(highest). Curves A, B, C and D represent the absorbance of the colored product obtained at varying levels of competing catalysts for this series A-D of successively increasing concentrations of analyte. The absorbance of the colored product for the lowest concentration of analyte, as shown in Curve A, is always, for a given concentration of competing catalyst, below that shown for the next lowest concentration of analyte for Curve B; which is in turn below that given for the higher concentration levels of analyte in C and D and so forth. The horizontal line at absorbence level X represents the level of detection possible with the naked eye—i.e. those reactions which produce detectable product of absorbance higher than X can be seen; those which produce product at concentration lower than that which will produce an absorbance of X cannot. As shown on the graph, Curves A-D cross the visibility line at successively lower concentrations of competing catalysts. Thus, at concentration level 1 of competing catalyst, even the analyte level represented by Curve A can be detected whereas at concentration of competing catalyst level 4, only the analyte level represented by the highest concentration (D) falls above the X cutoff line. A tabulation of these results is shown in Table 1 below.

TABLE 1

| Analyte | Competing Catalyst Concentration | | | |
| Concentration | 1 | 2 | 3 | 4 |
| --- | --- | --- | --- | --- |
| A | Y | N | N | N |
| B | Y | Y | N | N |
| C | Y | Y | Y | N |
| D | Y | Y | Y | Y |

Y = Yes (detectable)
N = No (not detectable)

Table 1 indicates that analyte levels A, B, C and D can be differentiated from each other entirely by their pattern of responses to varying levels of competing catalyst; thus level A gives a visible response only at competing catalyst level 1 whereas level B gives a visible response at competing catalyst levels 1 and 2 but not at 3 and 4. Analyte at level D gives a visible response at all levels of competing catalyst concentration.

Thus, in carrying out the method of the invention, the sample to be analyzed is divided into several portions each of which is then contacted with the necessary reagents and catalyst (or substrate) for the control/indicator reaction. Each portion is also contacted with the reagents and catalyst necessary for the competing reaction. By varying the amount of the competing catalyst the level of competion with the control/indicator reaction is also varied. Higher concentrations of analyte will be capable of carrying out the control/indicator reaction despite more effective depletion by the competing catalyst reaction, and the array of detectable versus undetectable reactions as a function of competing reaction catalyst or reactant will be characteristic of a particular analyte concentration.

In the alternative, the competing catalyst can be used in competition for the same substrate as that used by an enzyme analyte. Then, a fixed, limiting amount of this common substrate is added to the reaction mixture or reagent. Because it is unlikely that the enzyme analyte will catalyze a color-producing indicator reaction, a competing enzyme is chosen which does so. Under these circumstances, the color will be *less* when the concentration of analyte is higher. Of course, if the control reaction can still be used as indicator, this is preferred.

Of course, such an arrangement could form an alternative for substrate analysis or secondary analyte analysis as well—i.e. the control (constant reaction component addition) reaction may simply be used as a counterfoil for a competing/indicator reaction.

In one preferred embodiment of the present invention, separate containers are provided with equal amounts of a solution containing all of the necessary reactants and catalyst (or substrate) for effecting the control/indicator reaction and with quantities of solution containing reactants and varying amounts of catalyst reactants necessary for effecting the competing reaction. Dried reagents and catalysts which can be reconstituted with water may also be used. In either case, the reaction is essentially "wet" chemistry and only the mode of reagent supply differs. To this series of containers, which now contains fixed quantities of control/indicator reactant reaction components, and variable amounts of competing reaction components is added equal quantities of the sample to be assessed. After the requisite amount of time to permit the reactions to go to completion, the containers are observed to ascertain whether or not detectable product is in fact visible. By comparing the pattern of visibility/invisibility as a function of competing catalyst concentration to that obtained from a previously determined set of standard analyte concentrations, the analyte concentration of the test sample is then determined.

The times, temperatures, pH and other conditions operable and preferred for any particular embodiment will, of course, depend on the specific nature of the reagents and the catalyst used. In general, for reactions useful in clinical applications which involve assay of substrate compounds using enzymatic catalyst, the reactions are generally performed at around room temperature to around 37° C. at the pH optimum of the enzyme in question, usually around neutrality, and for reaction times appropriate to the level of substrate being tested. Preferably, the conditions of the reaction in terms of concentrations of materials are optimized so that dependable and produceable results can be obtained within a period of approximately 10 minutes or less, and the amount of competing catalyst adjusted so that a pattern of results is generated which permits assay over an approximately 10-fold concentration range of analyte.

In a still more preferred embodiment of the invention, a suitable support matrix, such as, for example, filter paper, silica gel plates, or other adsorbent is impregnated with a solution containing the reagents and catalyst (or substrate) for the indicator reaction distributed evenly over and throughout the support. This support is then subdivided into a series of test regions, preferably distributed about a central point but in any suitable configuration for ease of sample handling and reading. To each testing region is added a specific level, differing sequentially from region to region, of reagents and catalyst for effecting the competing reaction. Such a pattern could be obtained, for example, by blotting the support against a suitable template containing the various concentration levels of these materials in a patterned array of suitable containers. The resulting test sheet will be impregnated with a corresponding array of test positions which are capable of effecting the indicator reaction and which offer varying levels of competition for the analyte. All of those operations can be performed at a manufacturer's level, and the prepared matrix supplied to the end user.

Such systems are basically "dry" chemistry—i.e. the reactions take place without the use of solvent to reconstitute the components of the systems. The technology associated with preparing such systems is now well-established and fairly sophisticated. A number of such systems for qualitative and quantitative analysis are now available, from the familiar and seminal litmus paper developed in the 19th century, to the multi-layered and complex systems employed in instant photography. A number of dry chemistry systems based on, for example, color comparisons are also now available, such as reagent test strips for blood glucose or urine sugar content for use by diabetics. See, for example, Akai, T., et al, *Clinical Chemistry*, 29:1825 (1983) (urea nitrogen in saliva); Dappen, G. M . et al Ibid, 28:1159 (1982) (cholesterol in serum). Procedures for producing such dry chemistry support systems are well known in the art (Walter, B., *Anal Chem.*, 55:498A (1983).

The sample to be analyzed is then permitted to contact the various testing regions and the regions are scored according to whether or not visible product is noted. From the resulting pattern of positive and negative results, the concentration of analyte in the test sample can be assessed. Exact quantitative assignment of a numerical value for the concentration can be achieved by comparison with corresponding results from a series of appropriately diluted standards containing analytes in similar samples. I.e., precalibration with known samples is required.

Of course, as above, the incubation time, temperature and pH conditions for the method carried out on a solid matrix support will be dependent on the specific components of the system.

Figure 2:
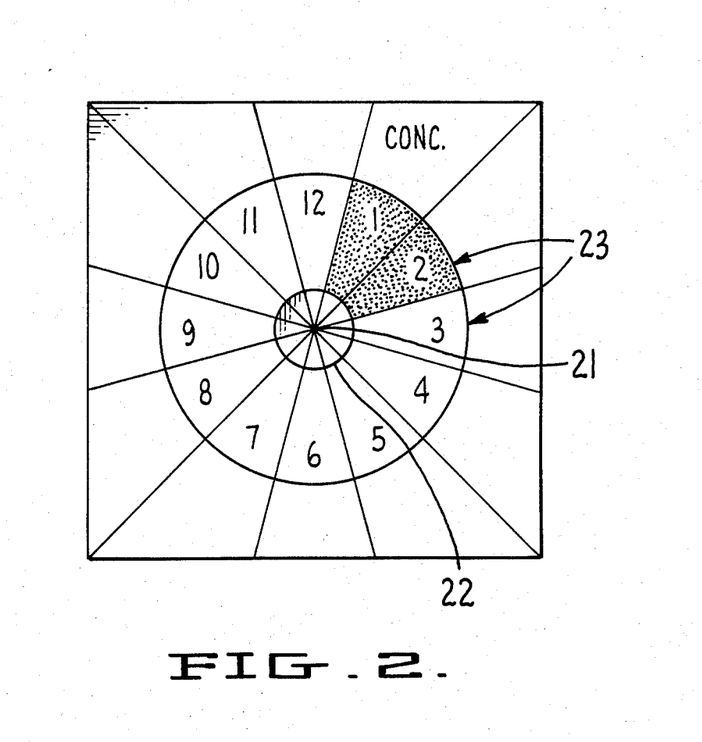
FIG. 2 diagrams the test matrix configuration for a "clock" analyzer.

A particularly preferred arrangement is that depicted in FIG. 2. The test matrix is divided into a series of arc segments, each of which contains equal amounts of indicator reaction components. As the series proceeds clockwise from 12 o'clock, each segment has a progressively greater amount of competing enzyme (along with additional reagents for the competing reaction if necessary). The sample is applied at the center 21, and allowed to diffuse through the matrix. If the sample contains interfering materials, e.g. red blood cells in a whole blood sample, it is desirable to interpose a semipermeable membrane 22 in a 360 degree arc such that the supernatant diffuses past the membrane and into the test areas 23. Depending on the concentration of analyte in the sample, segments will exhibit observable color through to later and later positions on the clock. Thus by reading the "time" at which the color stops, the range of amounts of analyte can be ascertained. A sample showing color up to only 2 o'clock is much less concentrated in analyte than one which shows color up to 11 o'clock.

C. Modification to utilize a secondary analyte

The foregoing methods and the preferred embodiments thereof are readily modified to adapt to analysis of a desired analyte by generating a secondary analyte serviceable as a substrate for both indicator and competing reactions. In order to insure specificity of the analysis, it is preferred that the desired analyte be a substrate in a reaction generating the secondary analyte which employs catalyst or enzyme limited in its effect to the desired primary analyte. The level of specificity required will, of course, vary with the nature of the contaminants present in the sample to be analyzed. The catalyst or enzyme will be sufficiently specific if it fails to utilize these contaminants.

When the analyte is, itself, an enzyme, a constant amount of substrate convertible to a secondary analyte is used. Thus, the secondary analyte is a product of the added substrate, and is in a concentration proportional to the enzyme analyte concentrtation. The remainder of the method is, then analogous to that described for analytes which are substrates.

To make the appropriate modification, the vessels of the above described preferred embodiment or testing regions of the more matrix of the still preferred embodiment above will also contain the suitable specific analyte reaction. These can be added or applied along with the control/indicator reaction components as these, too, will be used in fixed amounts for all portions of the sample. The advantage of utilization of a secondary metabolite is that the same test system can be used for a variety of analytic samples provided that a suitable spectrum of specific analyte reaction components can be found.

For example, $H_2O_2$ can be detected by competition between peroxidase and catalase controlled reactions as further described in the Examples below. A number of primary analytes can be used to generate the peroxide as a secondary analyte—e.g. glucose (glucose oxidase), cholesterol (cholesterol oxidase) and creatinine (creatinine amidino-hydrase and sarcosine oxidase); see Forsati, P., et al, *Clin. Chem*, 19:1494 (1983).

D. Kits and Supports

The materials useable in the methods of the invention can be supplied in convenient form as a kit or as a test matrix. Thus, the scope of the invention also includes such package configurations which offer the convenience of providing an organized system for carrying out the method of the invention. Enzymes or other catalysts and reactants useable in the methods of the invention can be supplied in solution or dried form and may be placed in a marketable kit in reaction vessels or as a diagramed matrix containing the appropriate testing regions. A particularly preferred embodiment comprises a series of reaction vials containing dried reagents for the indicator and if appropriate specific analyte reactions in equal amounts for each vessel and in varying amounts, the reactants and catalysts for the competing reaction. For use, vials can simply be activated by adding an appropriate amount of water, or of the sample solution directly. A suitable series of containers can be provided by oridinary vials, or by microtiter plates commonly in use in serial dilution based reactions in microbiology.

The dry chemistry alternative has been described in some detail above. A particularly useful configuration is the "clock" arrangement described in FIG. 2 and in Paragraph B. As the sample is applied to the center, it migrates uniformly to all test segments that radiate from this point and a constant amount of analyte to all segments is thus assured.

Figure 3:
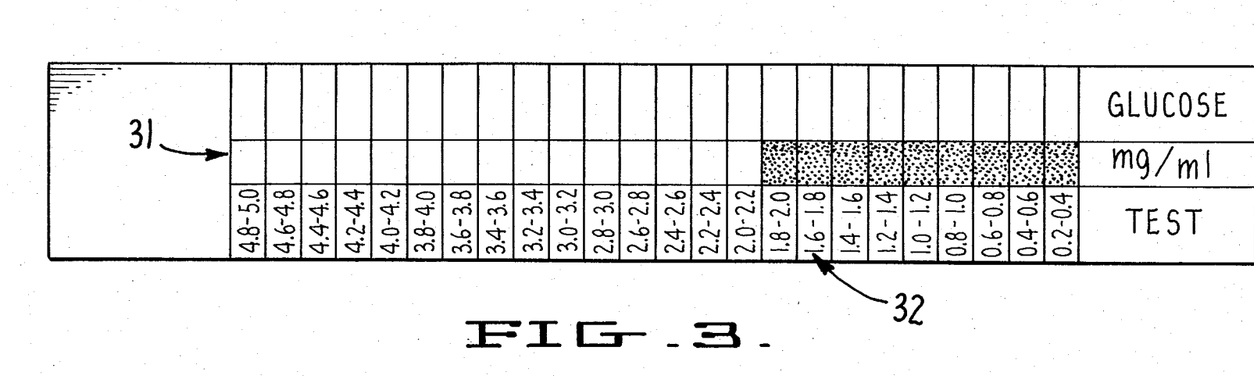
FIG. 3 diagrams the test matrix configuration for a "thermometer" analyzer.

Alternative configurations are also possible. For example, a "thermometer" as shown in FIG. 3 has increasing concentrations of competing reaction components in the segments as the test segments, 31, are arranged from right to left. If configured for analysis of a secondary analyte, equal amounts of specific analyte reaction catalyst will also be included in each segment. Samples or aliquots of the material to be tested are placed on each spot, and the ranges represented by color progression to a particular location denoted alongside (32). If, as is preferred, the control reaction is the indicator reaction, the more concentrated the sample, the farther to the left (as shown in FIG. 3) will extend the color bar. This configuration is perhaps less convenient than the "clock" for such semi-quantitative analysis because application of sample is required for each segment, and variations in volume due to precision limits of the application technique will cause variability in results.

(However, both "clock" and "thermometer" configurations are useful for use of a convenient display of *qualitative* results in a series of different tests. The matrix could contain in one segment the reagents for glucose assay, in another for ammonia, in another for urea, etc.)

In any event, whether formatted as wet chemical reactions in serial contained or as dry chemistry on a segmented matrix, the components of the test kits would comprise suitable reagents and catalysts for the control indicator, competing, and, if applicable, specific analyte reactions. Suitable indicator reactions include, for example, oxidation of hydrogen peroxide using peroxidase, oxidation of glucose with glucose oxidase coupled to a peroxidase dye producing reaction or a reaction of any analyte catalyzed by a specific enzyme which generates H+ in the presence of a pH indicator. Suitable competing catalysts include, for example, catalase (which competes with peroxidase for $H_2O_2$) or hexokinase (which competes with glucose oxidase for glucose). Provided a suitable indicator reaction is available, any enzyme which utilizes the same substrate is usable, and at least one such enzyme is almost certain to be found somewhere in the biosphere. Suitable specific analyte reaction catalysts include, for example, glucose oxidase and cholesterol oxidase, which generate peroxide from gluscose and cholesterol respectively.

Exemplary of schemes which take advantage of such reactions are as follows: the systems in A–E are for determination of substrate type analytes; F–H for determination of enzyme analytes.

A. Glucose Determination
Method 1: *Control/Indicator Reactions

-continued

*Competing reaction:

Method 2: *Control/Indicator Reactions

*Competing Reaction:

Method 3: *Specific Analyte Reaction

*Control/Indicator Reaction

*Competing reaction:

Method 4: *Specific Analyte Reaction

*Control/Indicator Reaction

*Competing reaction:

B. Cholesterol Determination
*Specific Analyte Reaction

*Control/Indicator Reaction

*Competing reaction:

C. Uric Acid Determination
*Specific Analyte Reaction

-continued

Uric Acid + $O_2$ $\xrightarrow{\text{Uricase}}$ $H_2O_2$ + Alantoin

*Control/Indicator Reaction
$H_2O_2$ + 4-Aminoantipyrene + p-Hydroxybenzoate $\xrightarrow{\text{Peroxidase}}$ $4H_2O$ + Quinoneimine Dye

*Competing reaction:

$2H_2O_2 \xrightarrow{\text{Catalase}} 2H_2O + O_2$

D. Triglyceride Determination

Method 1: *Specific Analyte Reactions

Triglycerides + $H_2O$ $\xrightarrow{\text{Lipase (EC 3.1.13)}}$ Glycerol + Free fatty acids Glycerol + ATP $\xrightarrow[\text{MgCl}_2]{\text{Lipase (EC 2.71.30)}}$ ADP + L-Glycerol-phosphate + $O_2$ L-α-Glycerol-phosphate $\xrightarrow{\text{L-glycerol-phosphate oxidase}}$ $H_2O_2$ + Dihydroxyacetone-phosphate

*Control/Indicator Reaction
$H_2O_2$ + 4-Aminoantipyrene + p-hydroxybenzoate $\xrightarrow{\text{Peroxidase (EC 1.11.1.7)}}$ $2H_2O$ + Quinoneimine Dye

*Competing reaction:

$2H_2O_2 \xrightarrow{\text{Catalase}} 2H_2O + O_2$

E. Creatinine Determination

*Specific Analyte Reaction

Creatinine + $H_2O$ $\xrightarrow{\text{Creatinine amidinohydrolase (EC 3.5.3.3)}}$ Urea + Sarcosine Sarcosine + $H_2O$ + $O_2$ $\xrightarrow{\text{Sarcosine oxidase (EC 1.5.3.1)}}$ Glycine + Formaldehyde + $H_2O_2$

*Control Indicator Reaction
$H_2O_2$ + 4-Aminoantipyrene + p-Hydroxybenzoate $\xrightarrow{\text{Peroxidase}}$ Quinoneimine dye + $4H_2O$

*Competing reaction:

$2H_2O_2 \xrightarrow{\text{Catalase}} 2H_2O + O_2$

F. Lactate Dehydrogenase (LDH) Determination

*Control Reaction

Pyruvate + $NADH_2$ $\xrightarrow{\text{LDH}}$ L-lactate + NAD
(with $NADH_2$ limiting)

*Competing/Indicator Reaction:

$NADH_2$ + Tetrazolium salt $\xrightarrow{\text{Diaphorase}}$ NAD + Formazan

G. Determination of Alanine Aminotransferase (ALT)

Control Reaction

L-glutamate + Pyruvate $\xrightarrow{\text{ALT}}$ L-Alanine + α-ketoglutarate
(with glutamate limiting)

*Competing/Indicator Reaction:

-continued

L-glutamate + $NAD^+$ + $H_2O$ $\xrightarrow{\text{Glutamate dehydrogenase}}$ α-ketoglutarate + $NH_3$ + $NADH_2$ $NADH_2$ + Tetrazolium salt $\xrightarrow{\text{Diaphorase}}$ NAD + Formazan H. Aspartate aminotransferase (AST) Determination

*Control Reaction

L-glutamate + Oxaloacetate $\xrightarrow{\text{AST}}$ L-aspartate + α-ketoglutarate
(with glutamate limiting)

°Competing/Indicator Reaction:

L-glutamate + $NAD^+$ + $H_2O$ $\xrightarrow{\text{Glutamate Dehydrogenase}}$ 2-oxoglutarate + $NH_3$ + $NADH_2$ $NADH_2$ + Tetrazolium salt $\xrightarrow{\text{Diaphorase}}$ NAD + Formazan

EXAMPLES

The following examples are meant to illustrate the invention, and not to limit it. Because of the wide variety and large number of reactant/catalyst combinations which can be used for each of the indicator, competing or specific analyte reactions, the invention is best illustrated by use of specific examples using specified embodiments of these reactants and catalysts. Accordingly, the examples below provide methods for analyzing for glucose or for cholesterol using a number of reactant catalyst compositions which are readily available in the art. However, depending on the nature of the sample to be analyzed, entirely different embodiments of such reagents and enzymes will be possible and, indeed, necessary.

1. Determination of Parameters to Provide A Glucose Test

In each of the examples below, the concentration of glucose tested is in the range of 0.01–0.3 moles per ml (i.e. about 1.8–54 g per ml). The assays are run at a reaction volume of 1.01 ml.

1.a. Glucose Oxidase as competing catalyst

To determine suitable concentration ranges for the competing catalyst and substrate concentration, the method of the invention was employed using as indicator reaction the conversion of glucose to glucose-6-phosphate in the presence of hexokinase, and the subsequent conversion of the glucose-6-phosphate to the corresponding carboxylic acid with the stoichiometric conversion of oxidized NAD+ to NADH. NADH is detectable by absorbance at 340 nm, thus, the level of absorbance at 340 nm can be used as an index of visibility. Further, the conversion of NAD+ to NADH can be utilized as a visible marker by supplying, in addition, a leuco dye and diaphorase. Thus, the reaction:

leuco dye + NADH (or NADPH) $\xrightarrow{\text{diaphorase}}$ $NAD^+$ (or $NADP^+$) + dye results in an observable color change proportional to the NADH generated (and to what is measured in this Example as 340 absorbance).

The competing reaction was the direct oxidation of glucose using, as competing catalyst, glucose oxidase. The results were determined at both ambient temperature and to 37° C.

Each reaction vessel contained in 1.01 ml total sample volume, 1.5 units per ml hexokinase
0.77 μmol/ml, ATP
1.9 units per ml glucose-6-phosphate dehydrogenase
0.91 μmol/ml NAD.

The mixture was buffered at pH 7.6.

These quantities represent an excess of reagents and sufficient catalyst to consume completely the levels of glucose supplied in the indicator reaction. The glucose is diluted 1:100 in the sample volume, so the concentrations are 0.01 of those shown in Tables 2-4. For each sample of glucose to be tested, a series of five vessels was used containing respectively 0, 62.5, 125, 250, and 500 units per ml of glucose oxidase.

The foregoing materials for the indicator reaction were supplied by reconstituting the Worthington StatzymeM Glucose Kit, catalog #27536. Glucose oxidase was obtained from Cal Biochem Boehringer and had a specific activity of 155 units per mg.

Tables 2a and 2b show the results at ambient temperature, and at 37° for a series of six glucose samples of various concentrations.

TABLE 2a $OD_{340}$ after 4 minutes at room temperature

| Glucose Concentration (mg/ml) | Glucose oxidase Conc. (U/ml) | | | | |
|---|---|---|---|---|---|
| | 0 | 62.5 | 125 | 250 | 500 |
| 0.31 | .107 | .080 | .085 | .074 | .064 |
| 0.62 | .217 | .134 | .170 | .145 | .122 |
| 1.25 | .418 | .320 | .291 | .280 | .237 |
| 2.5 | .861 | .594 | .621 | .530 | .424 |
| 5.0 | 1.523 | 1.226 | 1.149 | 1.002 | .815 |

TABLE 2b $OD_{340}$ after 10 minutes at 37° C.

| Glucose Concentration (mg/ml) | Glucose oxidase Conc. (U/ml) | | | | |
|---|---|---|---|---|---|
| | 0 | 62.5 | 125 | 250 | 500 |
| 0.31 | .108 | .081 | .086 | .073 | .062 |
| 0.62 | .220 | .178 | .175 | .137 | .119 |
| 1.25 | .383 | .314 | .294 | .267 | .236 |
| 2.5 | .710 | .617 | .647 | .510 | .432 |
| 5.0 | 1.734 | 1.139 | 1.168 | .946 | .710 |

These results indicate that in order to find a suitable cutoff visibility line, higher concentrations of glucose oxidase should be used, since only at very high concentrations of glucose does the oxidase appear to compete effectively with the indicator reaction. However, it is clear that concentration of glucose oxidase does affect the "visibility" of the indicator reaction, and that the amount of "visibility" is proportional to the level of glucose in the sample.

1.b. Hexokinase as competing catalyst

A similar determination was conducted reversing the roles of the indicator and competing reactions. The indicator reaction was supplied using Worthington StratzymeM catalog #27632 at concentrations which provide in each vessel sufficient catalyst and reactants to convert a suitable colorless dye precursor into visible dye. The dye is formed due to hydrogen peroxide generated by reaction of glucose with glucose oxidase. Thus, each vessel contains:

6.9 units per ml glucose oxidase,
0.5 μmol/ml 4-amino antipyrine,
21.8 μmole/ml sodium-p-hydroxybenzoate,
0.5 units per ml peroxidase, and
buffer to maintain the pH at 7.0.

Each series of vessels for a given glucose sample contains the following amounts of hexokinase and ATP, respectively per ml, 0 IU, 0 μmoles; 32.4 IU, 10 μmoles, 64.8 IU, 20 μmoles; 129.6 IU, 40 μmoles. The same sample levels of glucose were used as in paragraph 1.a above for the series set, i.e., the concentrations in Table 2 are diluted 1:100 in the test solution. The results were read at 500 nm (the absorbance maximum of the indicator reaction product) after 10 minutes at 37° C., and are shown in Table 3.

TABLE 3

| Glucose Concentration mg/ml | Concentration of Hexokinase IU/ml | | | |
|---|---|---|---|---|
| | 0 | 32.4 | 64.8 | 129.6 |
| 0.31 | 0.093 | 0.079 | 0.053 | 0.027 |
| 0.62 | 0.195 | 0.169 | 0.104 | 0.061 |
| 1.25 | 0.392 | 0.352 | 0.244 | 0.126 |
| 2.5 | 0.797 | 0.729 | 0.434 | 0.259 |
| 5.0 | 1.303 | 1.250 | 1.089 | 0.577 |

The results indicate that if a level of visibility at OD=0.1 is assumed, glucose levels in the range of 0.017-0.069 μmole/ml can be ascertained, using this embodiment. Of course, any sample of greater concentration can be used with proper dilution.

2. Assay for Glucose Using a Specific Analyte Reaction

Similar ranges of glucose concentrations were tested using a specific analyte reaction to produce hydrogen peroxide at the expense of glucose permitting an indicator reaction based on the decomposition of hydrogen peroxide catalyzed by peroxidase and simultaneous formation of a dye as set forth in paragraph 1.b. The competing reaction is the decomposition of hydrogen peroxide using variable levels of catalase.

To each reaction vessel was added a sufficient quantity of glucose oxidase and suitable peroxidase components as supplied by Worthington Statzyme catalog #27632 as set forth in 1.b. above to provide.

13.8 units per ml glucose oxidase;
1.0 μmole/ml 4-amino antipyrene;
43.6 μmole/ml sodium p-hydroxybenzoate; and
1 unit per ml peroxidase.

Each series of vessels contained catalase in concentrations of 0, 640, 1280, 2560, and 5120 units per ml. The concentration of glucose provided to each series of vessels was as set forth in paragraph 1. above, and the reaction was carried out at 37° C. and read after 10 minutes. The results are shown in Table 4a (again, the concentration is prior to the 100:1 dilution of the assay).

TABLE 4a

| Glucose Concentration mg/ml | Catalase (U/ml) | | | |
|---|---|---|---|---|
| | 640 | 1280 | 2560 | 5120 |
| 0.31 | 0.047 | 0.034 | 0.025 | 0.007 |
| 0.62 | 0.105 | 0.073 | 0.045 | 0.018 |
| 1.25 | 0.217 | 0.150 | 0.088 | 0.043 |
| 2.5 | 0.437 | 0.297 | 0.177 | 0.088 |

TABLE 4a-continued

| Glucose Concentration | Catalase (U/ml) | | | |
|---|---|---|---|---|
| mg/ml | 640 | 1280 | 2560 | 5120 |
| 5.0 | 0.860 | 0.601 | 0.352 | 0.185 |

TABLE 4b

| Glucose Concentration | Catalase (U/ml) | | | |
|---|---|---|---|---|
| mg/ml | 640 | 1280 | 2560 | 5120 |
| 0.31 | N | N | N | N |
| 0.62 | Y | N | N | N |
| 1.25 | Y | Y | N | N |
| 2.5 | Y | Y | Y | N |
| 5.0 | Y | Y | Y | Y |

Y = Yes (detectable)
N = No (undetectable)

These results show that the foregoing protocol is suitable for checking glucose concentrations 0.035–5 mg/ml (at the dilution of the assay) if a visibility level at OD=0.10 is assumed. Table 4b retabulates the results to indicate this.

3. Determination of Cholesterol

Worthington Reagents catalog #27571 test kit for cholesterol was used to provide the cholesterol esterase and oxidase for the analyte specific reaction as well as the peroxidase and reagents for the indicator reaction. Varying levels of catalase were again used as indicator reaction. Thus, each reaction vessel contained:

195.5 units per ml cholesterol oxidase,
554.2 mU/ml cholesterol esterase,
19.6 $\mu$mole/ml sodium cholate,
4.1 $\mu$mole/ml 4-amino antipyrine,
2.2 units per ml peroxidase, and
3.28 $\mu$mol/ml phenol plus sufficient buffer and surfactant to maintain proper reaction conditions.

Each series contained catalase at 0, 625, 1250, 2500, and 3750 units per ml. Cholesterol was supplied at 0, 1, 2, 3 and 5 ng/ml in the final reaction volume. Absorbance readings were taken at 500 nM after 2 minutes at 37KC, and are shown in Table 5 and FIG. 5, below. Absorbance readings were taken at 500 nm after 2 minutes at 37KC, and are shown in Table 5:

TABLE 5

| Cholesterol Concentration | Catalase (units/ml) | | | |
|---|---|---|---|---|
| ng/ml | 625 | 1250 | 2500 | 3750 |
| 1 | 0.062 | 0.013 | 0.012 | 0.004 |
| 2 | 0.110 | 0.014 | 0.011 | 0.009 |
| 3 | 0.161 | 0.033 | — | 0.012 |
| 5 | 0.234 | 0.044 | 0.029 | 0.015 |

Figure 4:
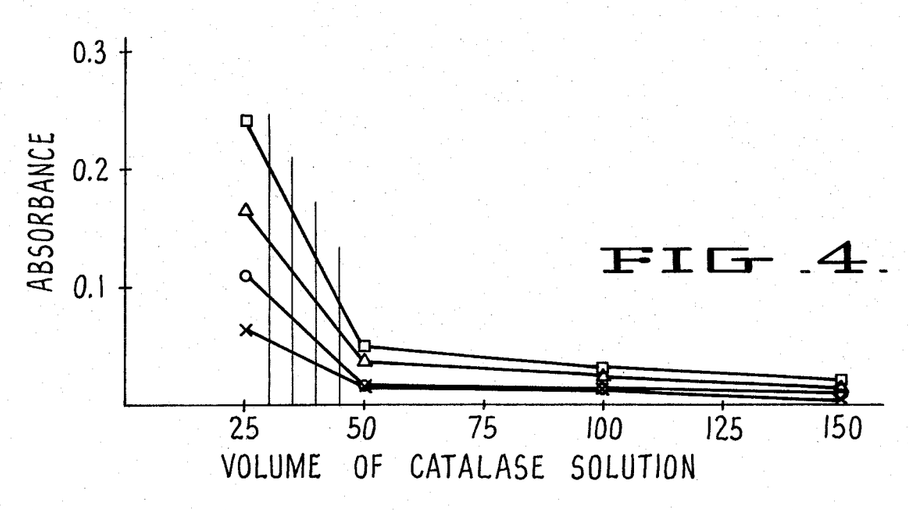
FIG. 4 is a graphic representation of cholesterol determination results.

FIG. 4 shows a graphic representation of these results. Comparison of this figure with the model set forth in FIG. 1 shows that the desired pattern is obtained.

4. Assay on Solid Matrix Support

The assay of example paragraph 2 was repeated on a support using Whatman #2 filter paper as a matrix. Glucose oxidase reacts specifically with glucose to form peroxide, and the indicator reaction takes advantage of the catalysis by peroxidase of dye formation by reaction with $H_2O_2$. The competing reaction is the decomposition of $H_2O_2$ using catalase.

As in paragraph 2, the specific analyte reaction and indicator reaction components were supplied by the Worthington Statzyme Glucose (500 nm) kit.

Reagent was made from the dry kit reagents in combination with catalase solution such that a 15 $\mu$l spot would contain:

0.028 U glucose oxidase
0.02 $\mu$mol 4-aminoantipyrine
0.88 $\mu$mol Na p-hydroxybenzoate
0.02 U peroxidase with pH7 buffer; and amounts of catalase varying from 9–187 units catalase. Glucose amounts applied varied between 3.1 $\mu$g and 50 $\mu$g. The reagent was applied in 15 $\mu$l spots, allowed to dry, 10 $\mu$l glucose then applied and the resulting color ranked on a scale of 0–10 as follows: wherein 1 is a trace color, 2 is visible purple color, 4 is moderate, 7 is intense and 10 is very intense. The papers were read after 3 minutes.

Assuming a yes-no cut-off between 1 and 2, and using 10 catalase concentrations in the range given above, the following results were obtained:

| Glucose Concentration in Applied Sample mg/ml | Ratio of Yes/No |
|---|---|
| 0.31 | 1/9 |
| 0.62 | 4/6 |
| 1.25 | 7/3 |
| 2.5 | 8/2 |
| 5.0 | 10/0 |

Thus, in the foregoing ranges, the pattern of results clearly distinguishes between the various glucose concentrations.

Changing the catalase concentration to the range 12.5–150 units in another Experiment "B" and to the range of 10–83 units in an Experiment "C" respectively produced similar results but with a higher desired visibility cut-off. Thus, for papers read after two hours and one hour respectively using a similar procedure to that above, but scoring respectively 4 as a yes, and <4 as no in Experiment B and 3 as a yes and <3 as a no, in Experiment C the following patterns were obtained:

| Glucose Concentration in Applied Sample | Y/N Ratio | |
|---|---|---|
| mg/ml | Expt B | Expt C |
| 0.31 | 1/6 | 2/5 |
| 0.62 | 1/6 | 3/4 |
| 1.25 | 2/5 | 5/2 |
| 2.5 | 4/3 | 7/0 |
| 5.0 | 5/2 | 7/0 |

Thus, the required digital pattern is obtainable using "dry chemistry" with a solid support.

5. Solid Matrix Supported Reaction for Glucose Detection With Hexokinase Competion In a manner similar to that set forth in paragraph 4, determinations of glucose were made except that hexokinase/ATP mixtures were substituted for catalase as the competing reaction. The results were scored as above. HK was supplied in amounts over the range 1–17 IU/ml; the ATP was added in fixed amount (170 μg) along with the components for the indicator reaction.

When read after 1 hour at room temperature, assuming visibility at 3 (yes) and no visibility at <3 (no), the results were as follows:

| Glucose Concentration in Sample Applied mg/ml | Ratio of Yes/No |
|---|---|
| 0.31 | 0/5 |
| 0.62 | 2/3 |
| 1.25 | 3/2 |
| 2.5 | 5/0 |
| 5.0 | 5/0 |

I claim:

1. A solid support matrix suitable for determining the concentration of an analyte in a sample, which matrix comprises:
   a support divided into a plurality of test portions, wherein each one of said test portions contains first reaction and second reaction components,
   said first reaction components including at least a first catalyst capable of reacting with said analyte in a first reaction the concentration of said first catalyst being the same in each one of said individual test portions,
   said second reaction component including at least a second catalyst capable of reacting with said analyte in a second reaction in competition with said first catalyst, the concentration of said second catalyst being different in each one of said test portions,
   wherein either said first reaction or second reaction is an indicator reaction which produces a detectable result, and the other of said first and second reactions is a non-indicator reaction which does not produce a detectable result,
   whereby when a sample containing said analyte is added to each of said test portions an array of test portions having different results is obtained, such that in test portions where the ratio of indicator reaction catalyst to non-indicator reaction catalyst is high, the result of the indicator reaction is detectable, and in test portions wherein said ratio is low, the result of said indicator reaction is not detectable,
   whereby the concentration of analyte in said sample is determinable by observing the point at which changeover from detectable to non-detectable indicator reaction occurs.

2. The matrix of claim 1 wherein the first reaction components are the components for the indicator reaction so that in test portions where the ratio of second to first catalyst is low, said indicator reaction is detectable and in test portions where the ratio is high, said indicator reaction is non-detectable.

3. The matrix of claim 1 wherein the second reaction components are the components for the indicator reaction so that in test portions where the ratio of second to first catalyst is high, said indicator reaction is detectable and in test portions where the ratio is low, said indicator reaction is non-detectable.

4. A solid support matrix suitable for determining the concentration of a catalyst-analyte in a sample, which matrix comprises:
   a support divided into a plurality of test portions, wherein each one of said test portions contains first reaction and second reaction components,
   said first reaction components including at least a substrate capable of reacting with said catalyst-analyte in a first reaction, the concentration of said substrate being the same in each one of said individual test portions,
   said second reaction component including at least a second catalyst capable of reacting with said substrate in a second reaction in competition with said catalyst-analyte, the concentration of said second catalyst being different in each one of said individual test portions,
   wherein either said first reaction or second reaction is an indicator reaction which produces a detectable result, and the other of said first and second reactions is a non-indicator reaction which does not produce a detectable result,
   whereby when a sample containing said catalyst-analyte is added to each of said test portions an array of test portions having different results is obtained, such that in test portions where the ratio of indicator reaction catalyst to non-indicator reaction catalyst is high, the result of the indicator reaction is detectable, and in test portions wherein said ratio is low, the result of said indicator reaction is not detectable,
   whereby the concentration of catalyst-analyte in said sample is determinable by observing the point at which changeover from detectable to non-detectable indicator reaction occurs.

5. The matrix of claim 4 wherein the second reaction components are components for the non-indicator reaction so that in test portions where the ratio of second catalyst to catalyst-analyte is low, said indicator reaction is detectable and in test portions where the ratio is high, said indicator reaction is non-detectable.

6. The matrix of claim 4 wherein the second reaction components are components for the indicator reaction so that in test portions where the ratio of second catalyst to catalyst-analyte is high, said indicator reaction is detectable and in test portions where the ratio is low, said indicator reaction is non-detectable.

7. A method for determining the concentration of an analyte in a sample comprising:
   dividing a sample into a plurality of individual test portions;
   combining each one of said plurality of test portions with first reaction and second reaction components,
   said first reaction components including at least a first catalyst capable of reacting with said analyte in a first reaction, the concentration of said first catalyst being the same in each one of said individual test portions,
   said second reaction components including at least a second catalyst capable of reacting with said analyte in a second reaction in competition with said first catalyst, the concentration of said second catalyst being different in each one of said individual test portions, wherein either said first reaction or second reaction is an indicator reaction which produces a detectable result, and the other of said first and second reactions is a non-indicator reaction which does not produce a detectable result, whereby an array of test portions having different results is obtained, such that in test portions where the ratio of indicator reaction catalyst to non-indicator reaction catalyst is high, the result of the indicator reaction is detectable, and in test portions wherein said ratio is low, the result of said indicator reaction is not detectable, whereby the concentration of analyte in said sample is determinable by observing the point at which changeover from detectable to non-detectable indicator reaction occurs.

8. The method of claim 7 wherein the first reaction is the indicator reaction so that in test portions where the ratio of second to first catalyst is low, said indicator reaction is detectable and in test portions where the ratio is high, said indicator reaction is non-detectable.

9. The method of claim 7 wherein the second reaction is the indicator reaction so that in test portions where the ratio of second to first catalyst is high, said indicator reaction is detectable and in test portions where the ratio is low, said indicator reaction is non-detectable.

10. The method of claim wherein said first and second reactions are conducted on a solid support matrix.

11. A method for determining the concentration of a catalyst-analyte in a sample comprising:

dividing a sample into a plurality of individual test portions;

combining each one of said plurality of test portions with first reaction and second reaction components, said first reaction components including at least a substrate capable of reacting with said catalyst-analyte in a first reaction, the concentration of said catalyst-analyte being the same in each one of said indiviual test portions, said second reaction component including at least a second catalyst capable of reacting with said substrate in a second reaction in competition with said catalyst-analyte, the concentration of said second catalyst being different in each one of said individual test portions, wherein either said first reaction or second reaction is an indicator reaction which produces a detectable result, and the other of said first and second reactions is a non-indicator reaction which does not produce a detectable result, whereby an array of test portions having different results is obtained, such that in test portions where the ratio of indicator reaction catalyst to non-indicator reaction catalyst is high, the result of the indicator reaction is detectable, and in test portions wherein said ratio is low, the result of said indicator reaction is not detectable, whereby the concentration of catalyst-analyte in said sample is determinable by observing the point at which changeover from detectable to non-detectable indicator reaction occurs.

12. The method of claim 11 wherein the first reaction is the indicator reaction so that in test portions where the ratio of second catalyst to catalyst-analyte is low, said indicator reaction is detectable and in test portions where the ratio is high, said indicator reaction is non-detectable.

13. The method of claim 11 wherein the second reaction is the indicator reaction so that in test portions where the ratio of second catalyst to first catalyst-analyte is high, said indicator reaction is detectable and in test portions where the ratio is low, said indicator reaction is non-detectable.

14. The method of claim 11 wherein said first and second reactions are conducted on a solid support matrix.

* * * * *